(12) United States Patent
Argal et al.

(10) Patent No.: US 9,370,416 B2
(45) Date of Patent: Jun. 21, 2016

(54) REFRACTIVE-DIFFRACTIVE LENS

(75) Inventors: Sanjay Ram Swaroop Argal, Vadodara (IN); Munavvar Tahir Hussain, Vadodara (IN)

(73) Assignee: Jagrat Natavar Dave, Vadodara (IN)

( * ) Notice: Subject to any disclaimer, the term of this patent is extended or adjusted under 35 U.S.C. 154(b) by 297 days.

(21) Appl. No.: 13/392,574

(22) PCT Filed: Aug. 25, 2010

(86) PCT No.: PCT/IB2010/053818
§ 371 (c)(1),
(2), (4) Date: Feb. 27, 2012

(87) PCT Pub. No.: WO2011/024125
PCT Pub. Date: Mar. 3, 2011

(65) Prior Publication Data
US 2012/0165932 A1    Jun. 28, 2012

(30) Foreign Application Priority Data

Aug. 27, 2009  (IN) .......................... 2058/CHE/2009
Feb. 2, 2010   (EP) ...................................... 10152384
Jun. 25, 2010  (MX) .................... MX/a/2010/007175
Jun. 28, 2010  (EG) ................................... 1110/2010

(51) Int. Cl.
*A61F 2/16*     (2006.01)
*G02C 7/00*     (2006.01)
*G02C 7/02*     (2006.01)
*G02B 5/18*     (2006.01)
*G02C 7/04*     (2006.01)

(52) U.S. Cl.
CPC ............ *A61F 2/1618* (2013.01); *G02B 5/1895* (2013.01); *G02C 7/042* (2013.01); *A61F 2/1654* (2013.01); *G02C 2202/20* (2013.01)

(58) Field of Classification Search
CPC ....... A61F 2/1618; A61F 2/1654; G02C 7/06; G02C 7/042; G02C 2202/20
USPC ................................ 623/6.27–6.28, 6.3–6.31
See application file for complete search history.

(56) References Cited

U.S. PATENT DOCUMENTS

| 4,162,122 A | 7/1979 | Cohen |
| 4,210,391 A | 7/1980 | Cohen |
| 4,338,005 A | 7/1982 | Cohen |
| 4,340,283 A | 7/1982 | Cohen |

(Continued)

FOREIGN PATENT DOCUMENTS

| EP | 1194797 | 4/2002 |
| WO | WO 2006/047698 | 5/2006 |
| WO | WO 2011/024125 | 3/2011 |

OTHER PUBLICATIONS

Communication Pursuant to Rules 70(2) and 70a(2) EPC and Reference to Rule 39(1) EPC Dated Mar. 7, 2011 From the European Patent Office Re. Application No. 10152384.3.

(Continued)

*Primary Examiner* — David H Willse
*Assistant Examiner* — Tiffany Shipmon

(57) ABSTRACT

A multifocal lens device is disclosed. The device comprises a lens body being formed with a plurality of concentric annular zones separated by slanted steps. The concentric zones effect both diffraction and refraction of incident light, while the steps are substantially devoid of any diffractive or refractive power.

36 Claims, 3 Drawing Sheets

(56) References Cited

U.S. PATENT DOCUMENTS

| | | | |
|---|---|---|---|
| 4,637,697 | A | 1/1987 | Freeman |
| 4,641,934 | A | 2/1987 | Freeman |
| 4,655,565 | A | 4/1987 | Freeman |
| 4,881,804 | A | 11/1989 | Cohen |
| 4,881,805 | A | 11/1989 | Cohen |
| 4,995,714 | A | 2/1991 | Cohen |
| 4,995,715 | A | 2/1991 | Cohen |
| 5,017,000 | A | 5/1991 | Cohen |
| 5,054,905 | A | 10/1991 | Cohen |
| 5,056,908 | A | 10/1991 | Cohen |
| 5,076,684 | A | 12/1991 | Simpson et al. |
| 5,089,023 | A | 2/1992 | Swanson |
| 5,116,111 | A | 5/1992 | Simpson et al. |
| 5,117,306 | A | 5/1992 | Cohen |
| 5,120,120 | A | 6/1992 | Cohen |
| 5,121,979 | A | 6/1992 | Cohen |
| 5,121,980 | A | 6/1992 | Cohen |
| 5,129,718 | A | 7/1992 | Futhey et al. |
| 5,144,483 | A | 9/1992 | Cohen |
| 5,344,447 | A | 9/1994 | Swanson |
| 5,699,142 | A | 12/1997 | Lee et al. |
| 6,008,942 | A | 12/1999 | Ogusu et al. |
| 6,536,899 | B1 | 3/2003 | Fiala |
| 7,377,641 | B2 | 5/2008 | Piers et al. |
| 2004/0252274 | A1 | 12/2004 | Morris et al. |
| 2006/0098162 | A1* | 5/2006 | Bandhauer et al. ........... 351/159 |

OTHER PUBLICATIONS

Communication Under Rule 71(3) EPC Dated Dec. 14, 2011 From the European Patent Office Re. Application No. 10152384.3.
European Search Report and the European Search Opinion Dated Dec. 2, 2010 From the European Patent Office Re. Application 10152384.3.
International Preliminary Report on Patentability Dated Oct. 26, 2011 From the International Preliminary Examining Authority Re. Application No. PCT/IB2010/053818.
International Search Report and the Written Opinion Dated Dec. 2, 2010 From the International Searching Authority Re. Application No. PCT/IB2010/053818.
Response Dated Feb. 17, 2011 to the Written Opinion of Dec. 2, 2010 From the International Searching Authority Re. Application No. PCT/IB2010/053818.
Response Dated Aug. 24, 2011 to European Search Report and the European Search Opinion of Dec. 2, 2010 From the European Patent Office Re. Application 10152384.3 and Communication Pursuant to Rules 70(2) and 70a(2) EPC and Reference to Rule 39(1) EPC of Mar. 7, 2011 From the European Patent Office Re. Application No. 10152384.3.
Response Dated Aug. 25, 2011 to Communication Pursuant to Rules 70(2) and 70a(2) EPC and Reference to Rule 39(1) EPC of Mar. 7, 2011 From the European Patent Office Re. Application No. 10152384.3.
Translation of Examination Report Dated Oct. 25, 2011 From the Instituto Mexican de la Propriedad Industrial Re. Application No. MX/a/2010/007175.
Sommerfeld "Optik", Vorlesungen über Theoretische Physik, XP00260894, IV: 212-215, Jan. 1, 1989.

\* cited by examiner

REFRACTIVE-DIFFRACTIVE LENS

RELATED APPLICATIONS

This application is a National Phase of PCT Patent Application No. PCT/IB2010/053818 having International filing date of Aug. 25, 2010, which claims the benefit of priority from Indian Patent Application No. 2058/CHE/2009, filed Aug. 27, 2009, European Patent Application No. 10152384.3, filed Feb. 2, 2010, Mexican Patent Application No. MX/a/2010/007175, filed Jun. 25, 2010 and Egyptian Patent Application No. 1110/2010, filed Jun. 28, 2010. The contents of all of the above documents are incorporated by reference as if fully set forth herein.

FIELD AND BACKGROUND OF THE INVENTION

The present invention, in some embodiments thereof, relates to optics and, more particularly, but not exclusively, to intraocular and contact lenses.

The human eye is a complex anatomical device, which facilitates interpretation of shapes, colors and dimensions of objects by processing the light they reflect or emit. Similarly to a camera, the eye is able to refract light and produce a focused image that can stimulate neural responses and provide the ability to see.

For the purpose of providing a self-contained document, following is a description of the principle of operation of the mammalian eye, in general, and of the cornea in particular. The iris regulates the amount of light admitted to the interior of the eye, the cornea and the lens focus the light rays from an object being viewed onto the retina which transmits the image of the object to the brain via the optic nerve. About 75% of the focusing is provided by the cornea, with the other 25% provided by the crystalline lens which may acquire variable focal lengths.

The cornea is the most anterior structure of the eye. Since it has to be transparent to allow light to enter the eye, there are no blood vessels in the cornea. The cornea is composed of collagen fibers packed together in an organized pattern, thereby providing the cornea its light transparent nature. The cornea has the highest concentration of nerve endings in the entire body, thus making it extremely sensitive to any kind of trauma.

The front view of the cornea is of an aspheric shape, where the vertical dimension is smaller than the horizontal dimension by about 1-2%. The anterior is typically about 11.7 mm in diameter.

The quality of vision depends on many factors including the size and shape of the eye, and the transparency of the cornea and lens. When age or disease causes the lens to become less transparent, vision deteriorates because of the diminished light which can be transmitted to the retina. This deficiency in the lens of the eye is medically known as a cataract. An accepted treatment for this condition is surgerical removal of the lens and replacement of the lens function by an intraocular lens (IOL).

Over the years, numerous types of IOLs have been developed for correcting vision deficiencies. Generally, such lenses operate accordion to one two basic optical principles: refraction and diffraction.

A typical IOL is manufactured from polymethyl methacrylate, has a diameter of about 5-7 mm, and is supported in the eye by the spring force of flexible loops called haptics. Other materials are also used, and there are a variety of lens style and haptic designs.

Multifocal lens has more than one point of focus. A bifocal, which is a type of multifocal, has two points of focus, one at distance and the other at near. In multifocal IOL the aim is to increase the range of distinct vision and hence to reduce the dependence on additional spectacle corrections. Rigid lenses that have two or more optical powers are used to divide the incident light between axially separated images. Overall image quality is affected by the number of lens powers, and the image quality of the focused component itself.

One type of multifocal IOL is diffractive multifocal IOL. A pair of diffraction orders is used to provide two lens powers simultaneously by using rigid implant. One power is used for distance vision and the other power is used for near vision. In both cases defocused light is also incident on the retina, but the human visual system is tolerant of contrast-related image variations and this does not appear to be a problem for most patients. The diffractive design utilizes the full aperture and is tolerant of pupil size variations and modest decentration.

Generally, a diffractive lens consists of any number of annular lens zones of equal area. Between adjacent zones optical steps are provided with associated path length differences which usually are absolutely smaller than a design wavelength. The area or size of the zones determines the separation between the diffractive powers of the lens; this separation increases with decreasing zone area. The optical path difference determines the relative peak intensities of the various diffractive powers. For example, when the optical path difference equals half the wavelength there are two principal diffractive powers, the zeroth and the first order diffractive power. For absolute path differences which are smaller than half the wavelength, the zeroth order power is dominant, while for optical path differences which are of order of one wavelength the first diffractive order power is dominant.

Also known are lenses which are based on refractive principles. Such refractive lenses typically include concentric zones of differing power.

U.S. Pat. No. 4,338,005 discloses a multiple focal power optical device which includes a plurality of alternating annular concentric zones. At least some of the zones include focal power means for directing incident parallel light to a first focal point, and at least some of the zones include focal power means for directing incident parallel light to a second focal point. The radius of the nth zone is proportional to the square root of n, and the radius of the first zone is proportional to the square root of the wavelength under consideration.

U.S. Pat. No. 5,089,023 discloses an intraocular optical implant which includes a refractive/diffractive lens having an anterior surface and a posterior surface and a generally anterior-posterior optical axis. At least one of the anterior and posterior surfaces of the lens has a diffractive lens profile covering about half the effective lens area of the lens.

U.S. Pat. No. 5,699,142 discloses a diffractive multifocal ophthalmic lens having an apodization zone that gradually shifts the energy balance from the near focus to the distance focus over a substantial portion of the lens so that the outer region of the lens directs all of its energy to the distance focus.

U.S. Pat. No. 6,536,899 disclose a multifocal lens including a plurality of annular zones. Each annular zone is divided into two annular sub-zones such that the refractive powers within the sub-zones exhibit at least two diffractive powers and at least one of the diffractive powers substantially coincides with the average refractive power of each annular zone.

Additional background art includes U.S. Pat. Nos. 4,881,805, 5,344,47, 7,377,641, 4,162,122, 4,210391, 4,338,005, 4,340,283, 4,995,714, 4,995,715, 4,881,804, 4,881,805, 5,017,000, 5,054.905, 5,056,908, 5,120,120, 5,121,979, 5,121,980, 5,144,483, 5,117,306, 5,076,684, 5,116,111, 5,129,718, 4,637,697, 4,641,934 and 4,655,565, and European Patent No. 1194797B1,

SUMMARY OF THE INVENTION

According to an aspect of some embodiments of the present invention there is provided a multifocal lens device. The device comprises a lens body being formed with a plurality of concentric annular zones separated by slanted steps. The concentric zones effect both diffraction and refraction of incident light, while the steps are substantially devoid of any diffractive or refractive power.

According to some embodiments of the invention the lens body is constituted as an ophthalmic intraocular lens.

According to some embodiments of the invention the lens body is constituted as a contact lens.

According to some embodiments of the invention the lens body is constituted as a spectacle lens.

According to some embodiments of the invention the lens body has an aspheric profile.

According to some embodiments of the invention the aspheric profile is characterized by a conic constant in a range of from about −1.1 to about −1.37, inclusive.

According to some embodiments of the invention the lens body concentric zones comprises at least 20 concentric zones.

According to some embodiments of the invention the lens body concentric zones comprises at most 30 concentric zones.

According to some embodiments of the invention each step has a width which is from about 0.17 microns to about 0.2 microns.

According to some embodiments of the invention the heights vary from about 1.83 micron at the center to about 0.09 micron at the edge.

According to some embodiments of the invention the slopes vary from about 84° at the center to about 25° at the edge.

According to some embodiments of the invention the overall effective refractive area of the lens body is less than 60% of the total effective area of the lens body.

According to some embodiments of the invention the lens body is made of a biocompatible material. According to some embodiments of the invention the biocompatible material is hydrophilic acrylic material.

According to some embodiments of the invention the diffractive power of the zones gradually decreases.

According to some embodiments of the invention the refractive power is substantially uniform across the lens body.

According to some embodiments of the invention the zones are substantially equal in area.

According to some embodiments of the invention the zones and the steps transmit at least 80% of incident light.

According to some embodiments of the invention the lens body is foldable.

According to some embodiments of the invention the device further comprises haptic means coupled to the lens body.

According to an aspect of some embodiments of the present invention there is provided a method. The method comprises forming on a substance a plurality of concentric annular zones separated by slanted steps. The concentric zones effect both diffraction and refraction of incident light, while the steps are substantially devoid of any diffractive or refractive power.

According to some embodiments of the invention the substance is a lens body, and the method serves for forming a lens device.

According to some embodiments of the invention the substance is a mold and the method serves for forming a lens mold for mass fabrication of lens devices. According to some embodiments of the invention the method further comprises casting a lens device using the lens mold.

According to some embodiments of the invention the plurality of concentric annular zones are formed by a computerized numeric controlled lathe.

According to an aspect of some embodiments of the present invention there is provided a method of treating vision of a subject. The method comprises implanting a multifocal lens device in an eye of the subject. The multifocal lens device has a ophthalmic intraocular lens body being formed with a plurality of concentric annular zones separated by slanted steps. The concentric zones effect both diffraction and refraction of incident light, while the steps are substantially devoid of any diffractive or refractive power.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1A:
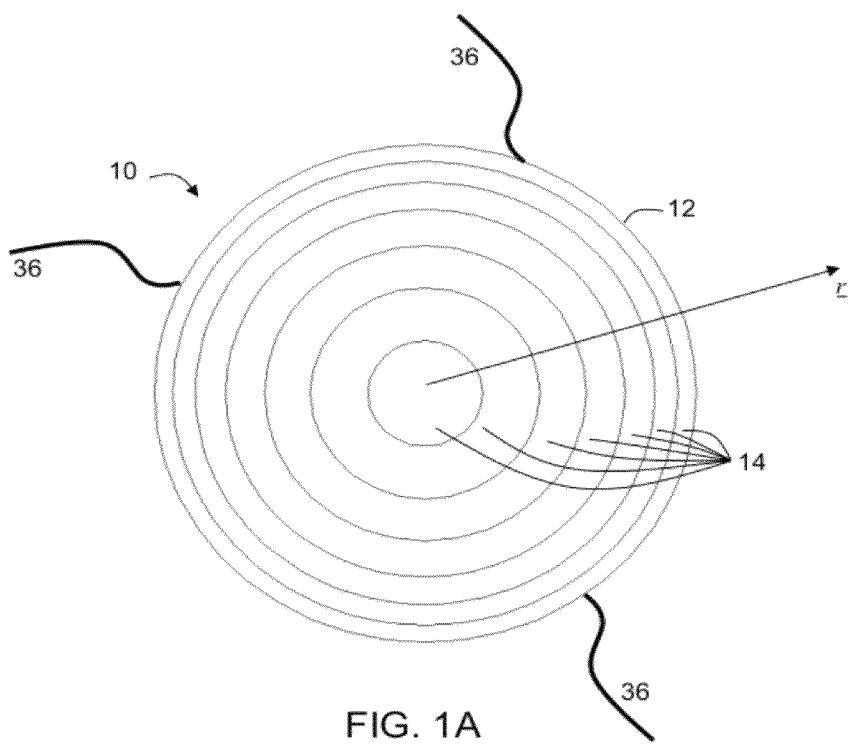
FIGS. 1A and 1B are schematic illustrations of a top view (FIG. 1A) and a profile view (FIG. 1B) of a multifocal lens device 10, according to various exemplary embodiments of the present invention.

The present invention, in some embodiments thereof, relates to optics and, more particularly, but not exclusively, to intraocular and contact lenses.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

When a ray of light moving in air and striking a surface of a light-transmissive substance at an angle $\alpha_1$ as measured from a normal to the surface, it is refracted into the substance at an angle which is determined by Snell's law, which is mathematically realized through the following equation:

$$n_A \sin \alpha_1 = n_s \sin \alpha_2$$

where $n_s$ is the index of refraction of the substance, $n_A$ is the index of refraction of the air, and $\alpha_2$ is the angle in which the ray is refracted into the substance. Similarly to $\alpha_1$, $\alpha_2$ is measured from a normal to the surface. A typical value of $n_A$ is about 1.

As used herein, the term "about" refers to ±10%.

Another optical phenomenon is diffraction which is the slight bending of light as it passes around the edge of an object, or at an opening thereof. The amount of bending depends on the size of the wavelength of light compared to the size of the opening or edge. If the opening is much larger than the light's wavelength, the bending will be almost unnoticeable. However, if the two are closer in size or equal, the amount of bending is considerable, and easily seen with the naked eye.

Optical effects resulting from diffraction are produced through the interaction of light waves originating from different regions of the opening causing the diffraction. Illustratively, one can view this interaction as one of two types of interferences: (i) a constructive interference when the crests of two waves combine to produce an amplified wave; and (ii) a destructive interference when a crest of one wave and a trough of another wave combine, thus canceling each other. A skilled artisan would, however, appreciate that there are many situations in which the interaction between the light waves is more complicated, e.g., when the light has a plurality of wavelengths.

The present Inventors exploit the refraction and diffraction phenomena for devising a multifocal lens device. Typically, the lens device of the present embodiments has diffractive power for enabling near vision and refractive power for enabling far vision. In various exemplary embodiments of the invention the lens device also enable intermediate vision, as further detailed hereinunder.

Figure 1B:
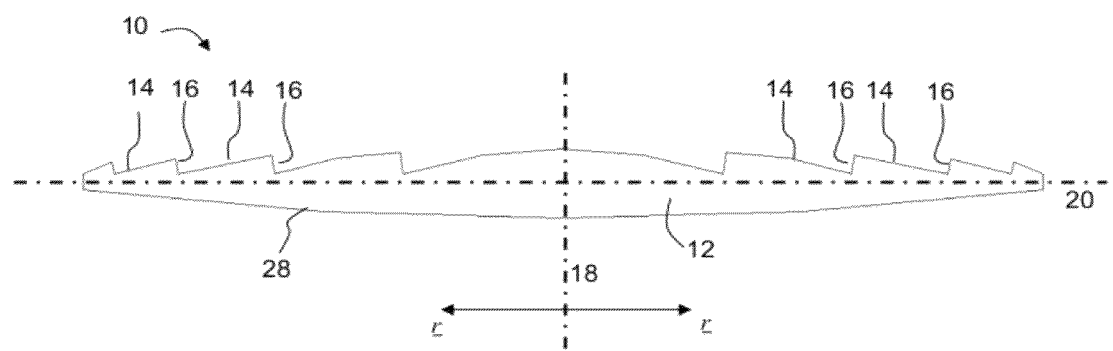

Referring now to the drawings, FIGS. 1A and 1B illustrate a top view (FIG. 1A) and a profile view (FIG. 1B) of a multifocal lens device 10, according to various exemplary embodiments of the present invention. Device 10 comprises a lens body 12 being formed with a plurality of concentric annular zones 14 separated by slanted steps 16 (shown better in FIG. 1B). The number of concentric zones is preferably at least 20, or at least 22 or at least 24 or at least 26 or at least 28, or at least 29. The number of concentric zones is preferably at most 30. In some embodiments of the present invention device 10 comprises 30 zones.

Device 10 can be used in more than one application. In some embodiments the device is implemented as intraocular lens device, in which case the lens body is constituted as an ophthalmic intraocular lens, in some embodiments the device is implemented as a contact lens, in which case the lens body is constituted as a contact lens, and in some embodiments the device is implemented as a spectacle lens in which case lens body is constituted as a spectacle lens.

In any of the above embodiments, lens body 12 preferably has an aspheric profile. Generally, the aspheric profile can be characterized by a conic constant in a range of from about −1.1 to about −1.37, inclusive.

Figure 4:
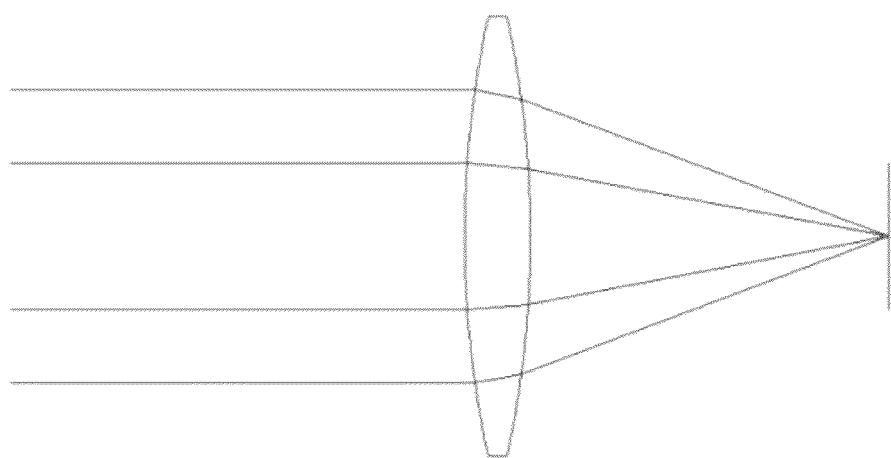
FIG. 4 is a schematic illustration of an aspheric lens body, according to various exemplary embodiments of the present invention.

A representative example of an aspheric lens body is illustrated in FIG. 4.

Lens body can be made of any material which is sufficiently transparent to visible light and which is suitable for optics. In various exemplary embodiments of the invention the lens body is made of biocompatible material, such as, but not limited to, hydrophilic acrylic material. In various exemplary embodiments of the invention the lens body is foldable. These embodiments are particularly useful when device 10 is used as an intraocular lens device or a contact lens device.

The device of the present embodiments differs from conventional lens devices in that substantially the entire contributions to the diffraction and refraction powers are in zones 14, whereas the contribution of steps 16 to diffraction and refraction powers is negligible or zero, even though they are slanted with respect to the optical 18 and transverse 20 axes of lens body 12. Thus, in various exemplary embodiments of the invention concentric zones 14 effect both diffraction and refraction of incident light, while steps 16 are substantially devoid of any diffractive or refractive power.

Figure 2A:
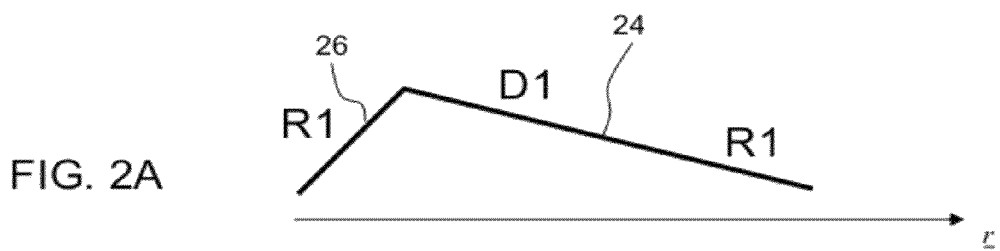
FIG. 2A is a schematic illustration of a single zone and slanted step of a conventional lens body.
Figure 2B:
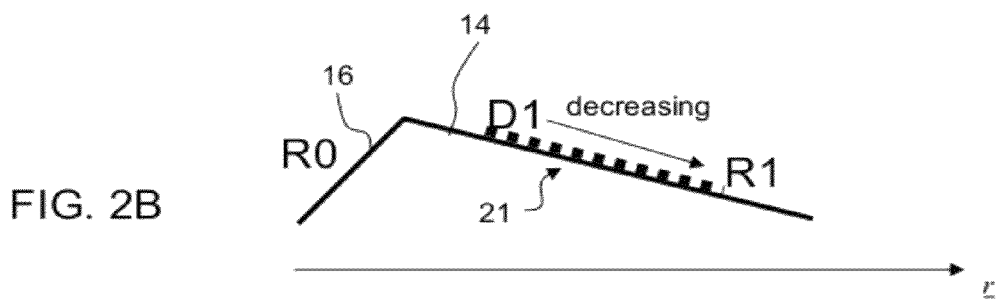
FIG. 2B is a schematic illustration of a single zone and slanted step of a lens body according to various exemplary embodiments of the present invention.

This advantage is illustrated in FIGS. 2A and 2B, which illustrate a single zone 24 and slanted step 26 of a conventional lens body (FIG. 2A) and a single zone 14 and slanted step 16 of lens body 12 (FIG. 2B). In FIGS. 2A-B, R1 and R2 represent refractive powers which generally equal the zeroth diffractive power, D1 represents the first order diffractive power and R0 represents a zero refractive power. In the conventional lens body, both the zones 24 and slanted steps 16 have optical power: step 16 has only a refractive power (R1) and zone 24 has both refractive (R2) and diffractive (D1) powers. In lens body 12, on the other hand, step 16 is substantially devoid of any optical (refractive or diffractive) power.

It is appreciated that whether or not there is optical power depends on the accuracy of the device which measures the optical power. As used herein, "substantially devoid of optical power" refers to zero optical power or optical power which is below 0.5 diopters, more preferably below 0.4 diopters more preferably below 0.3 diopters more preferably below 0.2 more preferably below 0.1 diopters.

Thus, every portion of lens body 12 has optical power (diffractive and/or refractive), but the contribution of this optical power generally comes form the zones and not the steps. The optical power of the zones is achieved by providing the zones with a finite radius of curvature relative to the transverse plane containing transverse axis 20 and/or with a secondary diffraction patterns 21 on their surface. However, the steps are preferably made planar, namely with infinite or very large radius of curvature.

The terms "refractive power" and "diffractive power" as used herein with respect to a particular optical element (either a section of lens body 12 or lens body 12 as a whole), refer to the dominant optical power of that element. Specifically, a particular optical element is said to have a refractive power if at this element the refractive power dominates the diffractive power, and particular optical element is said to have a diffractive power if at this element the diffractive power dominates the refractive power. If the refractive and diffractive powers are comparable, the element is said to have both optical powers.

In some embodiments of the present invention the diffractive power of the zones gradually decreases across each zone in the radial direction $\underline{r}$ (throughout this specification, underlined italic symbols represent vectors). This is illustrated in FIG. 2B for the case in which the diffractive power of the zone is the first order diffractive power. The advantage of gradually decreasing diffractive power is that it provides intermediate vision along with near and distance vision. Gradual decrease of the diffractive power across each zone can be achieved by changing the diffraction pattern across the zone.

The refractive power of device 10 is preferably substantially uniform across lens body 12. For example, in some embodiments of the present invention, each zone can have the same refractive power, with deviations of less that 10% or less than 5%. Additionally, the refractive power of the zone can be substantially uniform across the refractive section of this zone. The overall effective refractive area of lens body 12 is preferably small. In some embodiments of the present invention overall effective refractive area is less than 80% or less than 70% or less than 60% of the total effective area of lens body.

Figure 3:
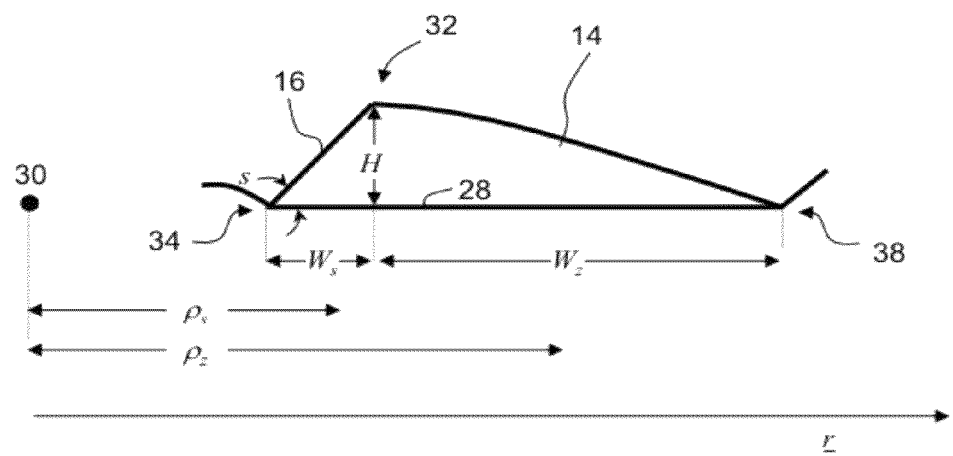
FIG. 3 is a schematic illustration of geometrical definition of a zone and a step adjacent thereto, according to various exemplary embodiments of the present invention.

FIG. 3 illustrates the geometrical definition of a zone 14 and a step 16 adjacent thereto. For clarity of presentation, FIG. 3 does not illustrate the entire lens body 12, however, the center of lens body 12 is shown at 30 for reference.

Step 16 is characterized by a radius $\rho_s$ (measured, e.g., from the center 30 of lens body 12 to the center of the step along radial direction $\underline{r}$), a slope s (measured, e.g., relative to the transverse plane containing transverse axis 20), a height H (measured, e.g., from the base 28 of lens body 12 to the tip 32 of the step), and a width $W_s$ (measured, e.g., from tip 32 to the end 34 of the previous zone along radial direction $\underline{r}$).

Zone 14 is characterized by a radius $\rho_z$ (measured, e.g., from the center 30 of lens body 12 to the center of the zone along radial direction $\underline{r}$), a width $W_z$ (measured, e.g., from tip 32 to the beginning 38 of the next step along radial direction $\underline{r}$) and a curvature (not shown in FIG. 3). The height H of step 16 also characterizes zone 14.

In some embodiments of the present invention the slope s and height H of a particular slanted step 16 are at least non-increasing functions of the radius $\rho_s$. For example, the slope and height can be decreasing functions of the radius. In other words, in this embodiment, the steps are ordered such that their slopes and heights are decreasing from center to edge. As a representative example for height decrease, the heights can vary from about 1.83 micron at the center of the lens body (where the radius $\rho_s$ is the smallest) to about 0.09 micron at the edge of the lens body (where $\rho_s$ is the largest). As a representative example for slope decrease, the slopes can vary from about 84° at center to about 25° at edge.

The decreasing functions of the radius of the radius can be expressed analytically. However, from a practical point of view these functions can be expressed as lookup tables. A representative example of such lookup table, for a lens body having of 30 zones and 30 steps is provided in the Example section that follows (see Table 1).

In some embodiments of the present invention steps 16 have generally the same width $W_s$, with about 10% or less deviation. Representative examples for width W of step 16 suitable for the present embodiments includes width ranging from about 0.17 microns to about 0.2 microns, or from about 0.18 microns to about 0.19 microns, inclusive. In some embodiments of the present invention all steps have widths which are either 0.18 microns or 0.19 microns.

Preferably, the zones 14 of lens body 12 are substantially equal in area, with deviation of less than 10% or less than 5%. This embodiment is advantageous since it reduces or eliminates halos and glare.

In some embodiments of the present invention device 10 further comprises haptic means 36 coupled to lens body 12 (see FIG. 1A). These embodiments are particularly useful when device 10 is used as an intraocular lens device, in which case haptic means 36 can be used for placing and optionally anchoring device 10 into the eye of the subject.

The lens body of the present embodiments provides high level of light transmission. In various exemplary embodiments of the invention the zones and steps transmit at least 75%, or at least 76%, or at least 77%, or at least 78%, or at least 79%, or at least 80% of incident light.

The use of zones and steps according to various exemplary embodiments of the present invention is particularly useful from the stand point of manufacturing process. Since the steps are substantially planer, the machining of the lens is substantially simpler compared to conventional lenses.

Additional advantages of the lens device of the present embodiments over conventional vision correcting lenses include, without limitation, reduced or no aberration to the optical system, reduced or no halos and light scattering, tolerated decentration and combination of intermediate vision with far and near vision. Further, when the device is used as an intraocular lens device or contact lens device, its aspheric shape fits the surface of cornea hence making the device suitable for many patients.

The lens device of the present embodiments can be fabricated in any technique known in the art. Generally, the present embodiments form on a substance a plurality of concentric annular zones separated by slanted steps, wherein the concentric zones effect both diffraction and refraction of incident light, while the steps are substantially devoid of any diffractive or refractive power. The substance on which the zones and steps are formed can be an unprocessed or partially processed lens body, in which case the formation of zones and steps serves for forming the lens device directly. Alternatively, the substance can be a mold, in which case the formation of zones and steps serves for forming a lens mold for mass fabrication of lens devices. In these embodiments, the lens device can be cased using the lens mold, as known in the art.

The formation of zones and steps may be done by any convenient manufacturing means, including, for example, a computer-controllable manufacturing device, molding or the like.

A "computer controllable manufacturing device" refers to a device that can be controlled by a computer system and that is capable of producing directly a lens body or a mold for producing a lens device. Any known, suitable computer controllable manufacturing device can be used in the invention. Exemplary computer controllable manufacturing devices includes, but are not limited to, lathes, grinding and milling machines, molding equipment, and lasers. In various exemplary embodiments of the invention a Computerized Numeric Controlled (CNC) lathe machine is used, such as the lathers marketed under the trade names DAC™ Vision, Optoform and CareTec.

The present embodiments also contemplate a method of treating vision of a subject in need thereof. The method comprises implanting a multifocal lens device in an eye of the subject, thereby treating the vision of the subject. The multifocal lens device is preferably device 10 as further detailed hereinabove. The method can be excited, for example, while or subsequently to a cataract surgery.

The word "exemplary" is used herein to mean "serving as an example, instance or illustration." Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments." Any particular embodiment of the invention may include a plurality of "optional" features unless such features conflict.

The terms "comprises", "comprising", "includes", "including", "having" and their conjugates mean "including but not limited to".

The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following example.

EXAMPLE

Reference is now made to the following example, which together with the above descriptions illustrates some embodiments of the invention in a non limiting fashion.

A prototype lens device was designed according to various exemplary embodiments of the present invention. The lens device included 30 zones and steps.

Figure 5A:
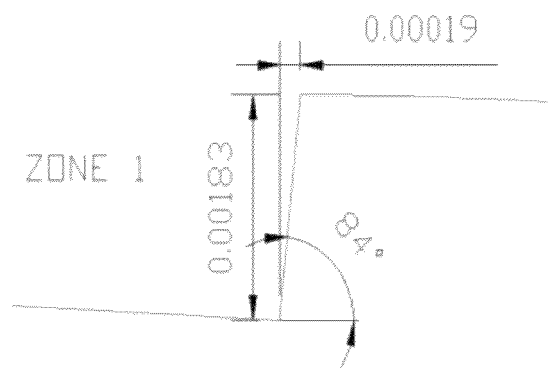
FIGS. 5A and 5B are schematic illustration of an outermost zone (FIG. 5A) and an innermost zone (FIG. 5B) of a prototype lens device designed according to various exemplary embodiments of the present invention.
Figure 5B:
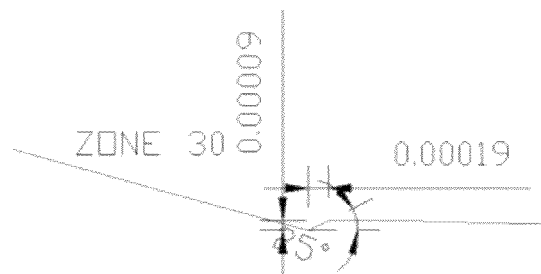

FIG. 5A illustrates the central (innermost) zone (referred to as zone 1), and FIG. 5B illustrates the peripheral (outermost) zone (referred to as zone 30). As shown, zone 1 has a step height H=1.83 microns and slope s=84°, and zone 30 has a step height H=0.09 microns and slope s=25°. Both zones exhibit diffractive for near vision and refractive power for far vision.

The values of step height H, step slope s and step width $W_s$ for each of the 30 steps is summarized in Table 1, below.

TABLE 1

| Zone No. | Step height [μm] | Step slope [degrees] | Step width [μm] |
|---|---|---|---|
| 1 | 1.83 | 84 | 0.19 |
| 2 | 1.77 | 84 | 0.19 |
| 3 | 1.71 | 84 | 0.18 |
| 4 | 1.64 | 83 | 0.19 |
| 5 | 1.57 | 83 | 0.19 |
| 6 | 1.51 | 83 | 0.19 |
| 7 | 1.45 | 83 | 0.19 |
| 8 | 1.40 | 83 | 0.18 |
| 9 | 1.32 | 82 | 0.18 |
| 10 | 1.26 | 81 | 0.19 |
| 11 | 1.19 | 81 | 0.18 |
| 12 | 1.16 | 81 | 0.19 |
| 13 | 1.09 | 80 | 0.19 |
| 14 | 1.01 | 80 | 0.18 |
| 15 | 0.94 | 79 | 0.19 |
| 16 | 0.90 | 79 | 0.18 |
| 17 | 0.90 | 79 | 0.18 |
| 18 | 0.82 | 77 | 0.19 |
| 19 | 0.77 | 76 | 0.19 |
| 20 | 0.70 | 75 | 0.19 |
| 21 | 0.64 | 73 | 0.19 |
| 22 | 0.60 | 72 | 0.19 |
| 23 | 0.51 | 70 | 0.19 |
| 24 | 0.46 | 68 | 0.19 |

TABLE 1-continued

| Zone No. | Step height [μm] | Step slope [degrees] | Step width [μm] |
|---|---|---|---|
| 25 | 0.41 | 65 | 0.19 |
| 26 | 0.36 | 62 | 0.19 |
| 27 | 0.30 | 58 | 0.19 |
| 28 | 0.20 | 46 | 0.19 |
| 29 | 0.14 | 36 | 0.19 |
| 30 | 0.09 | 25 | 0.19 |

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A multifocal lens device comprising:
    a lens body being formed with a plurality of concentric annular zones having surfaces separated by slanted steps having surfaces,
    wherein said surfaces of said concentric zones effect both diffraction and refraction of incident light, while said surfaces of said steps are substantially devoid of any diffractive or refractive power; and
    wherein each zone of at least one zone of said plurality of concentric zones has a diffraction pattern formed on a respective surface of said zone, such that a diffractive power of said surface of said zone gradually decreases across said surface of said zone.

2. The device of claim 1, wherein each step of said steps is characterized by a radius, a slope and a height, and wherein said slope and said height are at least non-increasing functions of said radius.

3. The device according to claim 1, wherein said lens body is constituted as an ophthalmic intraocular lens.

4. The device according to claim 1, wherein said lens body is constituted as a contact lens.

5. The device according to claim 1, wherein said lens body is constituted as a spectacle lens.

6. The device according to claim 1, wherein said lens body has an aspheric profile.

7. The device according to claim 6, wherein said aspheric profile is characterized by a conic constant in a range of from about −1.1 to about −1.37, inclusive.

8. The device according to claim 1, wherein said plurality of concentric zones comprises at least 20 concentric zones.

9. The device according to claim 1, wherein said plurality of concentric zones comprises at most 30 concentric zones.

10. The device according to claim 1, wherein each step of said steps has a width which is from about 0.17 microns to about 0.2 microns.

11. The device according to claim 1, wherein said heights vary from about 1.83 micron at said center to about 0.09 micron at said edge.

12. The device according to claim 1, wherein said slopes vary from about 84° at said center to about 25° at said edge.

13. The device according to claim 1, wherein an overall effective refractive area of said lens body is less than 60% of the total effective area of said lens body.

14. The device according to claim 1, wherein said lens body is made of biocompatible material.

15. The device according to claim 14, wherein said biocompatible material is hydrophilic acrylic material.

16. The device according to claim 1, wherein a refractive power is substantially uniform across said lens body.

17. The device according to claim 1, wherein said zones are substantially equal in area.

18. The device according to claim 1, wherein said zones and said steps transmit at least 80% of incident light.

19. The device according to claim 1, wherein said lens body is foldable.

20. The device according to claim 1, further comprising haptic means coupled to said lens body.

21. A method, comprising:
    forming on a substance a plurality of concentric annular zones having surfaces separated by slanted steps having surfaces,
    wherein said surfaces of said concentric zones effect both diffraction and refraction of incident light, while said surfaces of said steps are substantially devoid of any diffractive or refractive power; and
    wherein each zone of at least one zone of said plurality of concentric zones has a diffraction pattern formed on a respective surface of said zone, such that a diffractive power of said surface of said zone gradually decreases across said surface of said zone.

22. The method of claim 21, wherein said substance is a lens body, and the method serves for forming a lens device.

23. The method of claim 21, wherein said substance is a mold and the method serves for forming a lens mold for mass fabrication of lens devices.

24. The method of claim 23, further comprising casting a lens device using said lens mold.

25. The method according to claim 21, wherein said forming said plurality of concentric annular zones, is effected by a computerized numeric controlled lathe.

26. The method according to claim 21, wherein said plurality of concentric zones comprises at least 20 concentric zones.

27. The method according to claim 21, wherein said plurality of concentric zones comprises at most 30 concentric zones.

28. A method of treating vision of a subject, comprising:
    implanting a multifocal lens device in an eye of the subject, said multifocal lens device having a ophthalmic intraocular lens body being formed with a plurality of concentric annular zones having surfaces separated by slanted steps having surfaces,
    wherein said surfaces of said concentric zones effect both diffraction and refraction of incident light, while said surfaces of said steps are substantially devoid of any diffractive or refractive power; and
    wherein each zone of at least one zone of said plurality of concentric zones has a diffraction pattern formed on a respective surface of said zone, such that a diffractive power of said surface of said zone gradually decreases across said surface of said zone.

29. The method of claim 28, wherein each step of said steps is characterized by a radius, a slope and a height, and wherein said slope and said height are at least non-increasing functions of said radius.

30. The method according to claim 28, wherein said lens body has an aspheric profile.

31. The method according to claim 28, wherein said plurality of concentric zones comprises at least 20 concentric zones.

32. The method according to claim 28, wherein said plurality of concentric zones comprises at most 30 concentric zones.

33. The method according to claim 28, wherein said plurality of concentric zones comprises at least 20 concentric zones.

34. The method according to claim 28, wherein each step of said steps has a width which is from about 0.17 microns to about 0.2 microns.

35. The method according to claim 28, wherein said heights vary from about 1.83 micron at said center to about 0.09 micron at said edge.

36. The method according to claim 28, wherein said slopes vary from about 84° at said center to about 25° at said edge.

* * * * *